United States Patent
Tolkoff

(10) Patent No.: US 6,610,070 B1
(45) Date of Patent: *Aug. 26, 2003

(54) DISTAL END FOR LIGATING BAND DISPENSER

(75) Inventor: Marc Joshua Tolkoff, Brookline, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/544,590

(22) Filed: Apr. 6, 2000

Related U.S. Application Data

(63) Continuation of application No. 09/220,477, filed on Dec. 23, 1998, now Pat. No. 6,059,798, which is a continuation of application No. 08/869,055, filed on Jun. 4, 1997, now Pat. No. 5,853,416.

(51) Int. Cl.[7] .............................................. A61B 17/04
(52) U.S. Cl. ..................................................... 606/140
(58) Field of Search ................................ 606/140, 144, 606/139, 141, 146

(56) References Cited

U.S. PATENT DOCUMENTS

| | | | |
|---|---|---|---|
| 4,938,765 A | 7/1990 | Rasmusson | |
| 5,269,789 A | 12/1993 | Chin et al. | 606/140 |
| 5,320,630 A | 6/1994 | Ahmed | 606/140 |
| 5,356,416 A | 10/1994 | Chu et al. | 606/140 |
| 5,398,844 A | 3/1995 | Zaslavky et al. | 606/140 |
| 5,423,834 A | 6/1995 | Ahmed | 606/140 |
| 5,462,559 A | 10/1995 | Ahmed | 606/140 |
| 5,507,797 A | 4/1996 | Suzuki et al. | |
| 5,569,268 A | 10/1996 | Hosoda | |
| 5,624,453 A | 4/1997 | Ahmed | |
| 5,857,585 A | 1/1999 | Tolkoff et al. | |
| 5,968,056 A | 10/1999 | Chu et al. | |
| 6,099,535 A | * 8/2000 | Lamport et al. | 606/140 |

FOREIGN PATENT DOCUMENTS

| | | |
|---|---|---|
| EP | 0679368 | 11/1995 |
| WO | WO 97/45060 | 12/1997 |

* cited by examiner

*Primary Examiner*—Gary Jackson
(74) *Attorney, Agent, or Firm*—Kenyon & Kenyon

(57) ABSTRACT

A supporting structure for a ligating band dispensing device adapted to be coupled to a distal end of an endoscope comprises a rigid substantially cylindrical, transparent outer support surface adapted to receive a plurality of ligating bands thereon, wherein the support surface includes a distal portion extending from a distal end thereof proximally to a distal-most ligating band receiving area. A channel extends axially through the support surface from the distal end to a proximal end thereof, wherein an abutting surface is formed along at least a portion of a circumference of the channel to define a distal-most point of penetration of an endoscope received therein. A gripping surface extending around at least a portion of a circumference of the proximal end of the channel is sized so that, when an endoscope extends into the proximal end of the channel, the gripping surface frictionally couples the support surface to the endoscope.

7 Claims, 6 Drawing Sheets

DISTAL END FOR LIGATING BAND DISPENSER

RELATED APPLICATION

This application is a continuation of prior application Ser. No. 09/220,477, filed Dec. 23, 1998, now U.S. Pat. No. 6,059,798 which is a continuation of prior application Ser. No. 08/869,055, filed Jun. 4, 1997, now U.S. Pat. No. 5,853,416.

FIELD OF THE INVENTION

The invention relates generally to the field of tissue ligation, and more particularly to an improved distal end for a device for dispensing ligating bands.

BACKGROUND OF THE INVENTION

Physicians have used elastic ligating bands to treat lesions, including internal hemorrhoids and mucositis and for performing mechanical hemostasis. The object of such ligation is to position a ligating band, which is usually elastic, over the targeted lesion or blood vessel section by first stretching the band beyond its undeformed diameter and then drawing the tissue to be ligated within the band. Thereafter the band is released so that it contracts, applying inward pressure on the section of tissue caught within the band. The effect of the inward pressure applied by the band is to stop all circulation through the targeted tissue, thereby causing the tissue to die. The body then sloughs off the dead tissue or the dead tissue may be aspirated into an endoscope or a similar device.

U.S. Pat. No. 5,398,844 to Zaslavsky et al. ("the Zaslavsky patent"), which is incorporated herein by reference, describes a ligating band dispensing device including a substantially cylindrical support surface over which elastic ligating bands are stretched. The cylindrical support surface is typically attached to the distal end of an endoscope which is advanced into the body to a target area. A user then applies suction through the endoscope to draw the tissue to be ligated into the cylindrical support surface and releases a ligating band to contract around the tissue.

Previous ligating band dispensers allowed a user to dispense only a single ligating band at a time. That is, after a single ligating band was dispensed, if a user wanted to ligate another portion of tissue, the user would remove the device from the patient's body, load a new ligating band on the device and reinsert the device to the desired area within the patient's body. The device of the Zaslavsky patent, allows a user to place several ligating bands at desired locations without removing the device from the patient's body to reload ligating bands. However, as the number of ligating bands included on the distal end of these devices has been increased, the field of vision from the endoscopes to which these devices are normally coupled has been correspondingly decreased.

More specifically, as shown in FIGS. 1 and 2 a known support surface 2 around which several elastic ligating bands 4 are received is mounted on the distal end of an endoscope 6. This support surface 2 is preferably formed of a rigid material, for example polycarbonate. The rigidity of this support surface 2 is necessary to maintain the size of the distal opening of the support surface 2 as the support su face 2 is subjected to compressive forces from ligating bands 4 and from vacuum pressure used to draw tissue into a tissue receiving space 18 formed axially through the support surface 30. A proximal end of the support surface 2 is coupled to an elastic ring 8 formed of, for example, silicone. The elastic ring 8 grips the distal end of the endoscope 6 to frictionally couple the support surface 2 to the endoscope 6. A shoulder 10 formed at the juncture between the support surface 2 and the ring 8 maintains a predetermined separation between the distal-most surface 12 of the endoscope 6 and the distal end 14 of the support surface 2 to provide a space 18 within which the tissue to be ligated may be received. The space 18 is often substantially conical with a minimum diameter at a proximal end thereof of, for example, 0.375 inches and a maximum diameter at the distal end of the support surface of 0.5 inches. As the endoscope 6 is received only within the elastic ring 8 and does not extend into the rigid support surface 2, this support surface 2 may be coupled to endoscopes 6 of various diameters with no modification.

FIGS. 3 and 4 show cross-sectional views of other known support surfaces 2' and 2", each also being adapted to receive an endoscope so that the distal end 12 of the endoscope 6 abuts a proximal end surface 7 of the support surface 30. The distal end 12 of the endoscope 6 is received within the ring 8 but does not extend into the support surface 30. The space 18 within the support surface 2, which is of substantially uniform diameter throughout, is reserved only for receiving the tissue to be ligated. This is true for both the 8 ligating band receiving supporting surface 2' and the 5 ligating band receiving support surface 2".

Even if the support surface 2 is made of transparent material, the breadth of the visual field of an optical device 16 (shown by the dotted lines in FIG. 2) included in the endoscope 6 is limited by the extent to which the ligating bands 4 extend distally of the distal end 12 of the endoscope 6. And, as the number of ligating bands 4 is increased, the distal extension of the ligating bands 4 is also increased, resulting in a corresponding decrease in the extent of the visual field.

SUMMARY OF THE INVENTION

The present invention is directed to a supporting structure for a ligating band dispensing device being adapted to be coupled to a distal end of an endoscope. The supporting structure comprises a rigid substantially cylindrical, transparent support surface adapted to receive a plurality of ligating bands thereon, wherein the support surface includes a distal portion extending from a distal end thereof proximally to a distal-most ligating band receiving area. A channel extends axially through the support surface from the distal end to a proximal end thereof and an abutting surface formed along at least a portion of a circumference of the channel defines a distal-most point of penetration of an endoscope received within the channel. A gripping surface, extending around at least a portion of a circumference of the proximal end of the channel sized so that, when an endoscope extends into the proximal end of the channel, the gripping surface frictionally couples the support surface to the endoscope.

BRIEF DESCRIPTION OF THE DRAWINGS

The invention will be more readily understood through the following detailed description, with reference to the accompanying drawings, in which.

Figure 1:
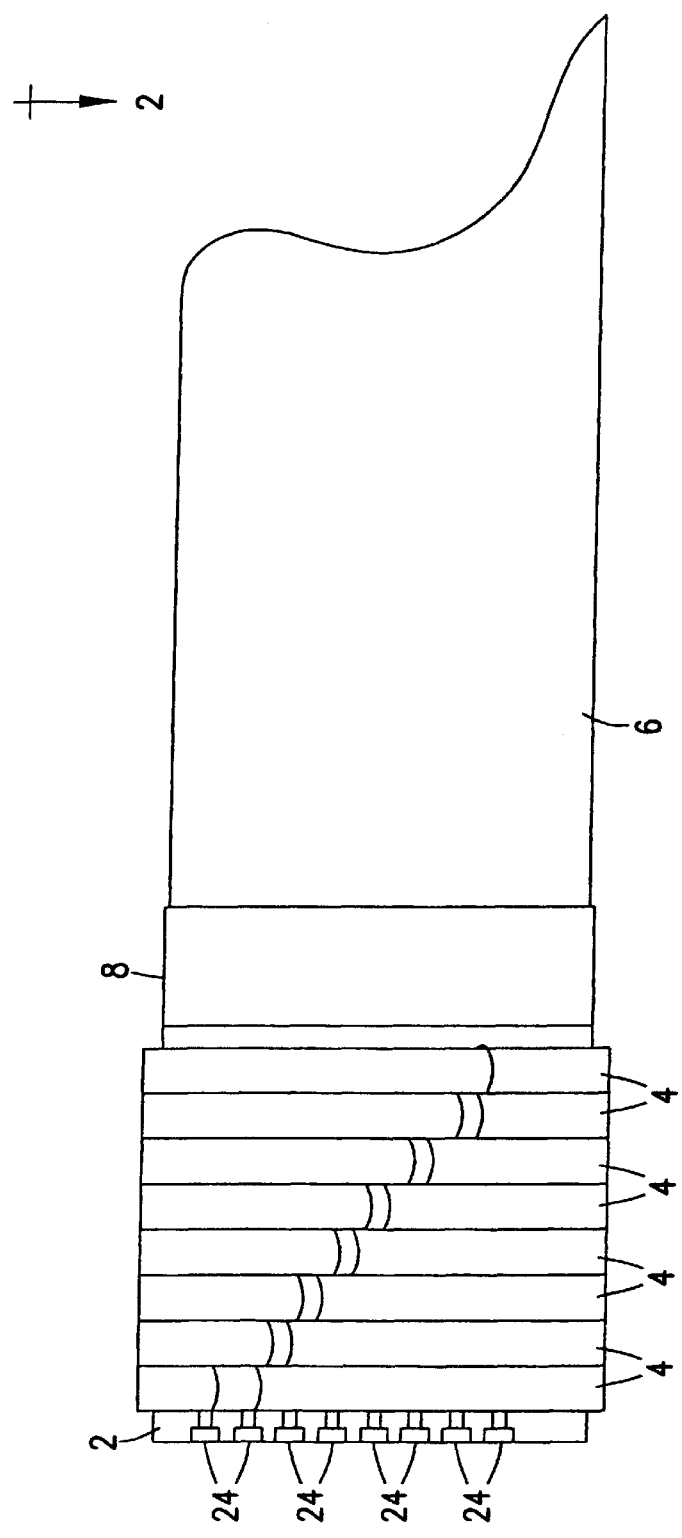
FIG. 1 is a perspective view of a known distal end of a ligating band dispensing device.
Figure 2:
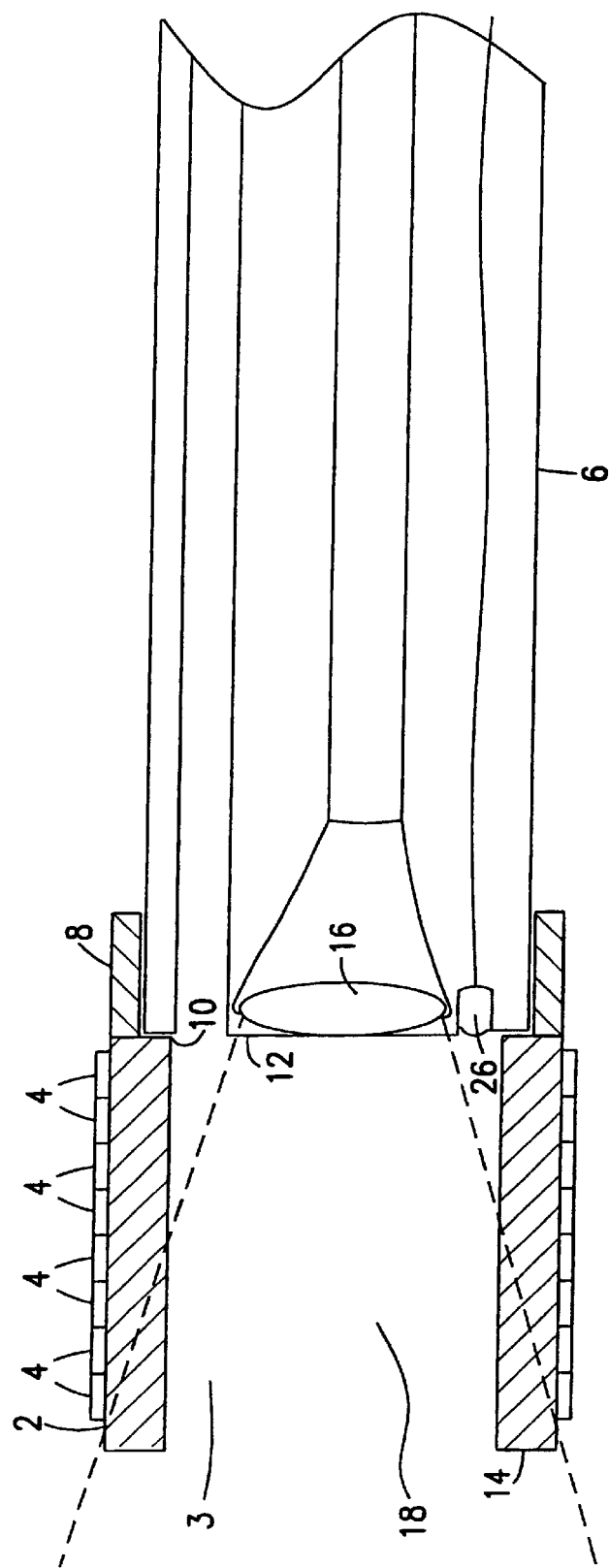
FIG. 2 is a cross-sectional view of the ligating band dispensing device of FIG. 1, taken along line 2—2 of FIG. 1.
Figure 3:
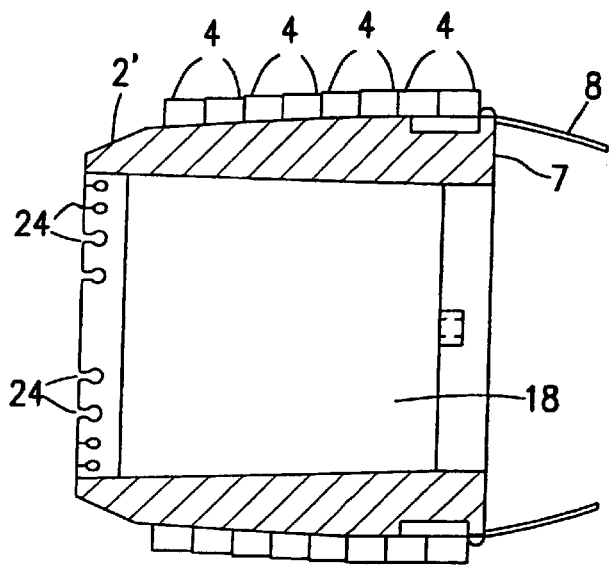
FIG. 3 is a cross-sectional view of a second prior art support surface.
Figure 4:
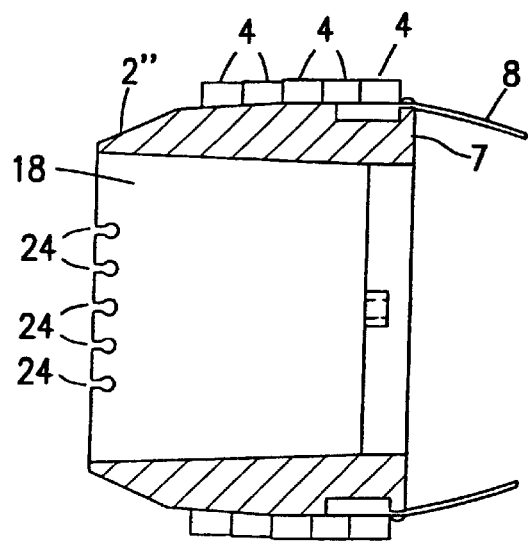
FIG. 4 is a cross-sectional view of a third prior art support surface.
Figure 5:
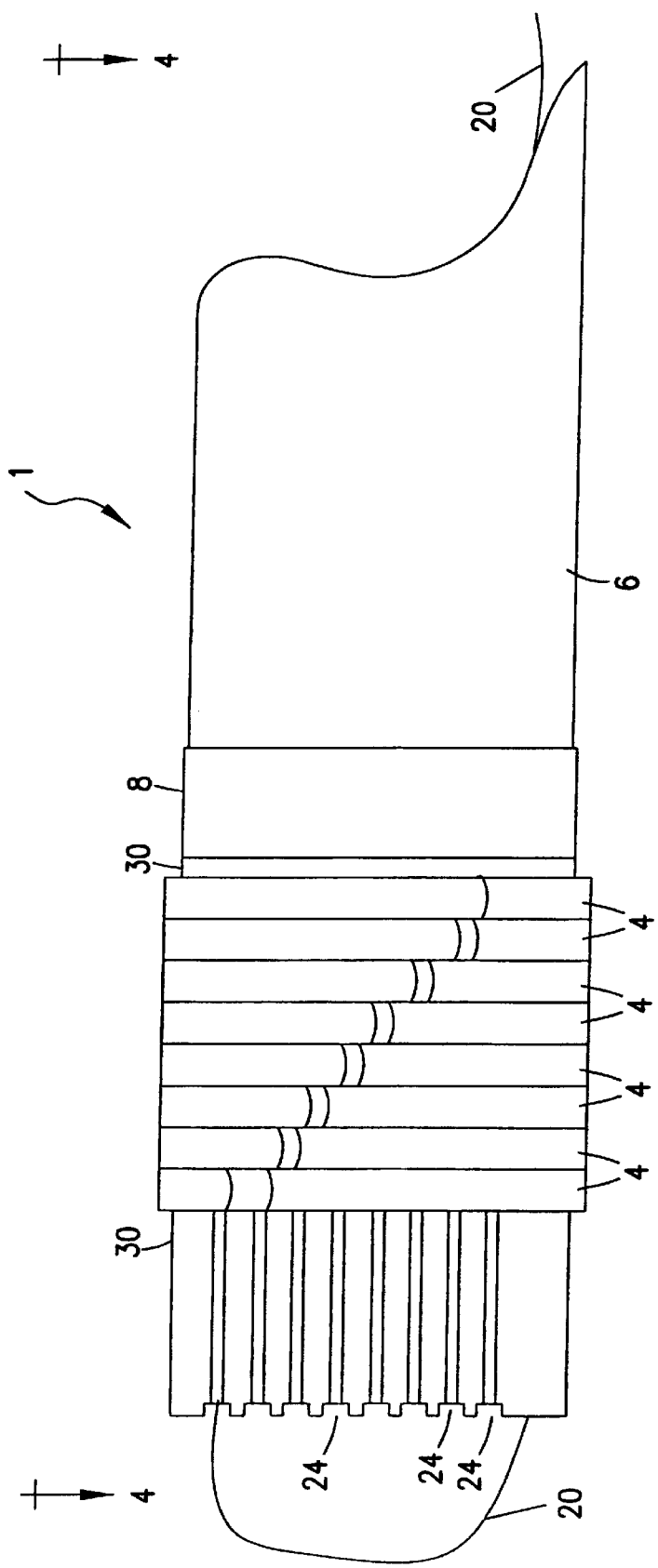
FIG. 5 is a perspective view of a distal end of a ligating band dispensing device according to a first embodiment of the present invention.
Figure 7:
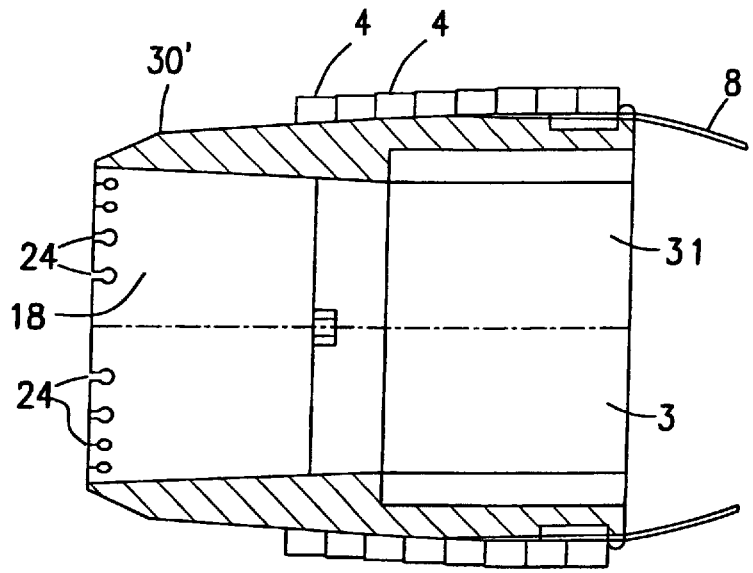
Figure 8:
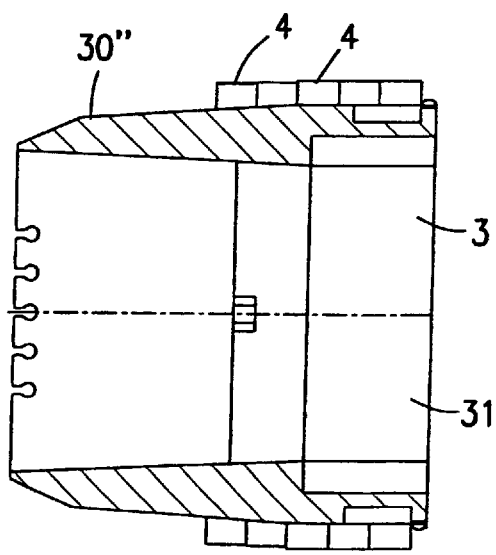

FIG: 6 is a cross-sectional view of the ligating band dispensing device of FIG. 5, taken along line 4—4 of FIG. 5;

FIG. 7 is a cross-sectional view of a ligating dispensing device according to a second embodiment of the invention; and FIG. 8 is a cross-sectional view of a ligating dispensing device according to a third embodiment of the invention.

DESCRIPTION OF THE PREFERRED EMBODIMENT

As illustrated in FIG. 5, a device 1 according to a first embodiment of the present invention includes a substantially cylindrical support surface 30 coupled to an elastic ring 8. A central bore 3 which extends through the support surface 2 and the elastic ring 8, in operation, receives the distal end of an endoscope 6. A plurality (8 in this case) of ligating bands 4 are received around the support surface 30 with a trigger line 20 wrapping around each of the ligating bands 4 in a repeating pattern. The support surface 30 and the support surface 30' of FIG. 7 for receiving 8 ligating bands 4 thereon will preferably be between 0.5 and 0.8 inches in length and may preferably be between 0.65 and 0.75 inches in length. While the support surface 30" of FIG. 8 may preferably be between 0.45 and 0.65 inches in length and is more preferably between 0.5 and 0.6 inches in length. Of course, those skilled in the art will understand that the length of the support surface may need to be varied depending on the thickness of the ligating bands (in a direction distal to proximal) received thereon. The ligating bands 4 are received on the support surface 30 so that a distal-most band 4 is separated from a distal end 14 of the support surface 30 by an area 15 which is, except for the trigger line 20, substantially free from visual obstructions. The support surface 30 is preferably substantially transparent. However, those skilled in the art will understand that at least the area 15, which preferably extends 0.2–0.3" should be transparent.

The trigger line 20 extends from a proximal end accessible to a user, through a lumen 22 in the endoscope 6 to pass through the central bore 3 and out to the support surface 30 via a first one of a plurality of grooves 24. The trigger line 20 then extends across the support surface 2, passes over the distal-most of the ligating bands 4 and wraps underneath this ligating band 4 to extend back into the first groove 24. The trigger line 20 then loops under the distal end 14 of the support surface 30 and passes through a second groove 24 adjacent to the first groove, passes under the distal-most band 4, wraps around this band 4 and passes under and around a second band immediately proximal to the distal-most band 4. The trigger line 20 continues over the second band 4 and passes back under the distal-most band 4 to extend to the second groove 24, returning from the second groove 24 to wrap over and around the second band 4, under the third band 4, etc. This pattern is repeated until the trigger line 20 extends around each of the ligating bands 4 received on the support surface 30. Of course, the arrangement of the trigger line 20 may be varied substantially so long as it is arranged so that a user is permitted to release each of the plurality of ligating bands 4 one at a time at each of a corresponding plurality of locations within the patient. Thus, for example, a separate trigger line 20 may be provided for each of the ligating bands 4 or a single line 20 may be divided at some point between the user and the support surface 30 into a plurality of filaments each of which is coupled to a respective ligating band 4.

The endoscope 6 extends past the juncture between the ring 8 and the support surface 30 to a shoulder 10 formed at a portion of the central bore 3 within the support surface 30. This shoulder 10 may preferably be located beneath one of the distal-most of the ligating bands 4 and is most preferably located so that, prior to releasing any ligating bands, the shoulder is beneath the third ligating band (counting distal to proximal) preferably between 0.35 and 0.5", and more preferably approximately 0.38" from the distal end of the support surface 30. This shoulder 10 prevents the endoscope 6 from moving past a distalmost position within the central bore 3, to create a substantially unobstructed space 18 extending from the distal end 14 proximally to the distal end of the endoscope 6. This space 18, which is dimensioned similarly to that of the support surface 2 described above, is separated at the shoulder 10 from an increased diameter endoscope receiving portion 31 of the bore 3 which preferably has a diameter of between 0.4 and 0.5 inches depending upon the diameter of the endoscope 6 which is to be received therein. The space 18 provides an area into which tissue to be ligated may be drawn so that a ligating band 4 released from the support surface 30 will encircle and grip the tissue to the extent necessary for the band 4 to be maintained in position on the tissue after the tissue has been released. That is, the tissue is drawn into the space 18 by known means such as, for example suction or a gripping mechanism (not shown) provided via the lumen 22. Thus, the placement of the endoscope 6 within the rigid support surface 30 and the extension of the support surface 30 distally beyond the distal-most ligating band 4 allow the space 18 to extend distally of the distal-most band 4.

Figure 6:
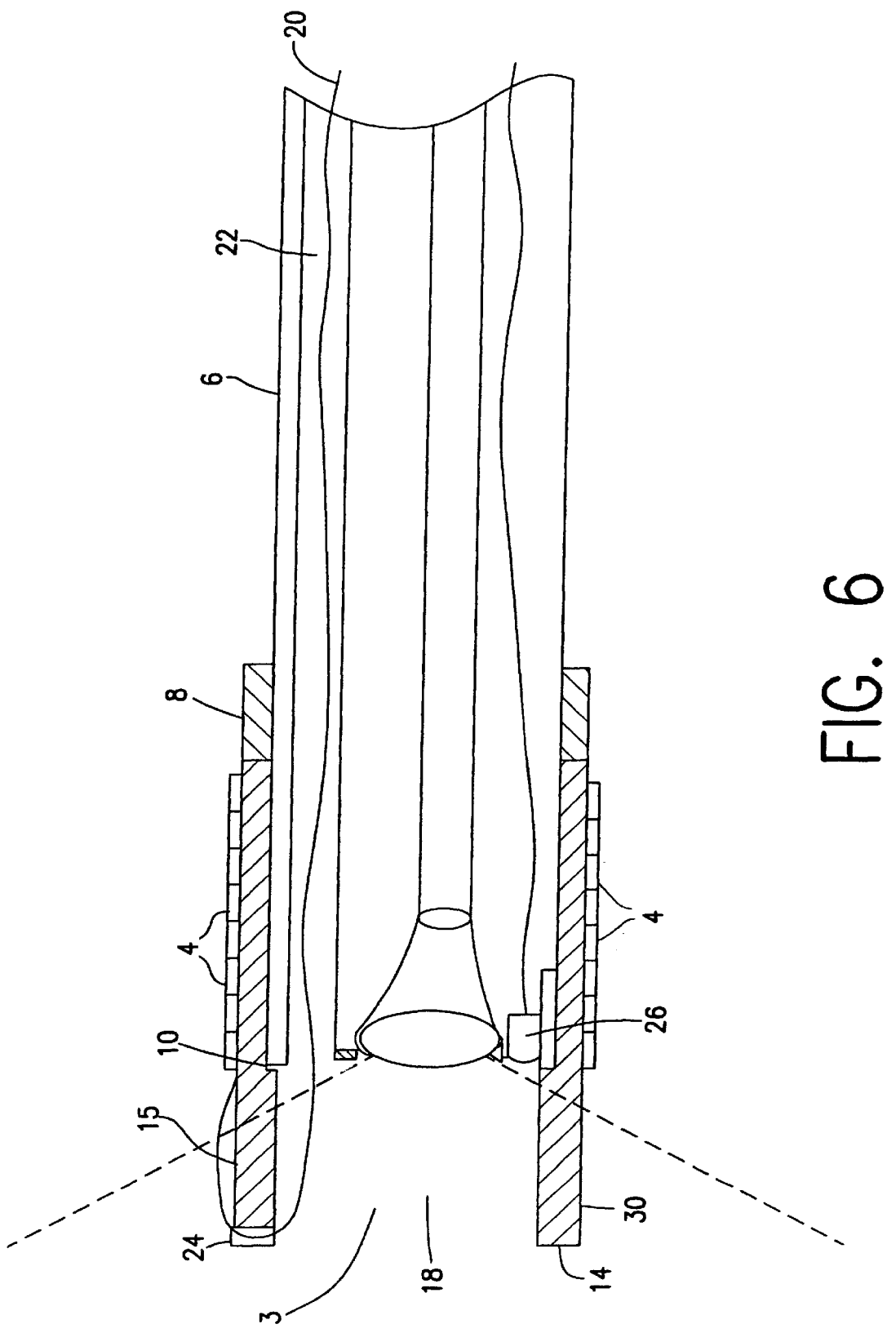

As noted above, the distal end of the endoscope 6 includes an optical device 16 and a light source 26 which allow a user to view the area adjacent to the distal end of the device 1. The placement of the endoscope 6 within the rigid support surface 30 and the consequent placement of the tissue receiving space 18 distally toward the distal-most band 4 (or distally past all of the ligating bands 4), allows the field of vision of the optical device 16 (shown by the dotted lines in FIG. 6) to be increased relative to that obtained with an endoscope 6 seated proximal to the juncture between the ring 8 and the support surface 30. Those skilled in the art will understand that an increase of nearly 2 to 1 over prior placement positions of the endoscope may be obtained with this arrangement. Of course, this increase of the field of vision is achieved only when the support surface 30 is formed of a transparent material which may preferably be polycarbonate.

As described above, the elastic ring 8 of the support surface 30 grips the endoscope 6 to prevent if from becoming separated from the support surface 30. However, those skilled in the art will understand that in order to maintain a proper fit of the endoscope 6 within the rigid support surface 2, or to accommodate larger endoscopes 6, sizing the endoscope receiving portion 31 of the central bore 3 to correspond to the diameter of the distal end of a particular endoscope 6 will provide a more secure and stable mating with the support surface 30.

In operation, a plurality of ligating bands 4 are placed,on the support surface 30 with the trigger line 20 threaded between the bands 4 as described above. Then an endoscope 6 is passed into the endoscope receiving portion 31 of the central bore 3 via an opening formed in the proximal end of the elastic ring 8 until a distalend of the endoscope 6 contacts the shoulder 10 and the trigger line 20 extended from the proximal end of the endoscope 6 through the central bore 3 to the ligating bands 4 (preferably via the lumen 22). The endoscope 6 is then inserted into a patient and advanced, under visual observation (via optical device 16) until the distal end 14 of the support surface 30 is adjacent to a portion of tissue to be ligated. The user then draws the tissue into the space 18 by, for example, advancing a gripping device (not shown) through the lumen 22 and grasping the tissue, or by applying suction through the lumen 22. When the tissue is in a desired position within the space 18, a user draws the trigger line 20 proximally through the lumen 22 until the distal-most ligating band 4 is released from the support surface 30 to ligate the tissue. As described in the Zaslavsky patent, the trigger mechanism of a ligating device incorporating a support surface according to the present invention will preferably provide the user with a tactile indication that a band 4 has been released. Thereafter, the user releases the tissue by withdrawing the gripping device or stopping application of the vacuum pressure and then visually guides the endoscope 6 to a second location within the patient. When the support surface 30 is located adjacent to a second portion of tissue to be ligated, the user repeats the process described above, releasing a second of the plurality of ligating bands 4. The second of the plurality of ligating bands 4 is preferably, after release of the first of the plurality of ligating bands 4, the distal-most ligating band 4 received on the support surface. The remaining ligating bands 4 may then be released one at a time, starting with the distal-most remaining ligating band 4 and progressing to the proximal-most band 4. Thus, the device 1 allows a user to ligate or more portions of tissue without removing the device 1 from the patient while providing the user with improved control of the endoscope 6 resulting from the expanded visual field.

The support surface 30" of FIG. 8 differs from the support surfaces 30 and 30' only in that it is shorter as it is intended to receive only 5 ligating bands thereon. Of course, those skilled in the art will understand that increased numbers of ligating bands 4 may be received on a support surface as described simply by lengthening the endoscope receiving portion 31 of support surface to the extent that the increase in length of the support surface does not result in excessive irritation to the patient or to difficulties in inserting the device into a body lumen.

There are many modifications of the disclosed embodiments which will be apparent to those of skill in the art. It is understood that these modifications are within the teaching of the invention which is to be limited only by the claims appended hereto.

What we claim is:

1. A supporting structure for a ligating band dispensing device, the supporting structure extending substantially along a longitudinal axis thereof from a proximal end adapted to be coupled to an endoscope to a distal end, the supporting structure comprising:

a rigid support surface, a distal portion of which extends proximally from the distal end of the supporting structure to a distal-most ligating band receiving area, at least the distal portion being substantially transparent;

a plurality of elastic ligating bands received around a portion of the support surface extending proximally from the distal-most ligating band receiving area;

a channel extending axially through the supporting structure from the distal end to the proximal end; and position fixing means defining a distal-most point of penetration of a distal end of an endoscope received in the channel distally of a proximal-most one of the ligating bands.

2. The supporting structure according to claim 1, wherein the position fixing means includes an endoscope abutting surface extending into the channel.

3. The supporting structure according to claim 2, wherein the endoscope abutting surface projects radially into the channel and extends around at least a portion of an inner diameter of the channel.

4. The supporting structure according to claim 1, wherein the support surface extends at least 0.5" from the distal end to the proximal end thereof.

5. The supporting structure according to claim 1, wherein the distal portion is at least 5 mm in length.

6. The supporting structure according to claim 1, wherein the distal end of the support surface includes a plurality of grooves formed therein for receiving a trigger line.

7. The supporting structure according to claim 3, wherein the abutting surface is positioned along the longitudinal axis substantially aligned with a distal end of the distal-most ligating band.

* * * * *